(12) United States Patent
Kobayashi et al.

(10) Patent No.: US 11,951,092 B2
(45) Date of Patent: *Apr. 9, 2024

(54) AGENT FOR PREVENTING OR TREATING BRAIN ATROPHY

(71) Applicant: FUJIFILM Toyama Chemical Co., Ltd., Tokyo (JP)

(72) Inventors: Hiroshi Kobayashi, Tokyo (JP); Yoshihiko Matsumoto, Tokyo (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/617,739

(22) PCT Filed: Jun. 1, 2018

(86) PCT No.: PCT/JP2018/021223
§ 371 (c)(1),
(2) Date: Nov. 27, 2019

(87) PCT Pub. No.: WO2018/221729
PCT Pub. Date: Dec. 6, 2018

(65) Prior Publication Data
US 2020/0215030 A1 Jul. 9, 2020

(30) Foreign Application Priority Data

Jun. 2, 2017 (JP) .............................. JP2017-109885
Jun. 30, 2017 (JP) .............................. JP2017-128472
Jul. 27, 2017 (JP) .............................. JP2017-145100

(51) Int. Cl.
*A61K 31/397* (2006.01)
*A61K 9/00* (2006.01)
*A61P 25/28* (2006.01)

(52) U.S. Cl.
CPC .......... *A61K 31/397* (2013.01); *A61K 9/0053* (2013.01); *A61P 25/28* (2018.01)

(58) Field of Classification Search
CPC ...... A61K 31/397; A61K 9/0053; A61P 25/28
See application file for complete search history.

(56) References Cited

U.S. PATENT DOCUMENTS

| | | | |
|---|---|---|---|
| 6,489,481 B1 | 12/2002 | Keith et al. | |
| 7,087,594 B2 | 8/2006 | Saitoh et al. | |
| 8,119,625 B2* | 2/2012 | Iwakami | A61K 31/397 514/210.19 |
| 10,238,632 B2 | 3/2019 | Yano | |
| 11,541,033 B2 | 1/2023 | Kobayashi et al. | |
| 11,548,878 B2 | 1/2023 | Yano et al. | |
| 2005/0070521 A1 | 3/2005 | Saitoh et al. | |
| 2005/0250843 A1 | 11/2005 | Nakada et al. | |
| 2006/0194781 A1 | 8/2006 | Saitoh et al. | |
| 2006/0205709 A1 | 9/2006 | Kimura et al. | |
| 2009/0093453 A1 | 4/2009 | Iwakami et al. | |
| 2009/0209512 A1* | 8/2009 | Iwakami | C07D 409/12 548/950 |
| 2010/0261752 A1 | 10/2010 | Beattie et al. | |
| 2011/0124631 A1 | 5/2011 | Koenig et al. | |
| 2011/0224180 A1 | 9/2011 | Pruss et al. | |
| 2012/0028953 A1 | 2/2012 | Roughley et al. | |
| 2015/0045345 A1 | 2/2015 | Inaba et al. | |
| 2015/0166472 A1 | 6/2015 | Kim et al. | |
| 2015/0203472 A1 | 7/2015 | Ceccarelli et al. | |
| 2016/0324851 A1 | 11/2016 | Friedhoff et al. | |
| 2017/0129915 A1 | 5/2017 | Tohda et al. | |
| 2017/0165227 A1 | 6/2017 | Takahashi et al. | |
| 2018/0153855 A1 | 6/2018 | Yano | |
| 2018/0369194 A1 | 12/2018 | Kano et al. | |
| 2020/0085787 A1 | 3/2020 | Kobayashi et al. | |
| 2020/0108048 A1 | 4/2020 | Kobayashi et al. | |
| 2020/0155505 A1 | 5/2020 | Kobayashi et al. | |
| 2021/0137880 A1 | 5/2021 | Kobayashi et al. | |
| 2021/0198245 A1 | 7/2021 | Yano et al. | |
| 2023/0346745 A1 | 11/2023 | Kobayashi et al. | |

FOREIGN PATENT DOCUMENTS

| | | |
|---|---|---|
| CN | 101432280 A | 5/2009 |
| CN | 104159583 A | 11/2014 |
| EP | 1 437 353 A1 | 7/2004 |
| EP | 3 100 725 A1 | 12/2016 |
| JP | 2002-528489 A | 9/2002 |
| JP | 2011-513374 A | 4/2011 |

(Continued)

OTHER PUBLICATIONS

William Jagust Brain—A Journal of Neurology 2016: 139; 23-30. (Year: 2016).*
Healthline "Brain Atrophy", updated on Mar. 29, 2019 https://www.healthline.com/health/brain-atrophy. (Year: 2019).*
Hirata et al Journal of Pharmacology and Experimental Therapeutics 2005, 314, 252-259. (Year: 2005).*
Kimura et al., T-817MA, a neurotrophic agent, ameliorates the deficts in adult neurogenesis and spatial memory in rats infused i.c.v. with amyloid-beta peptide, 2009, British Journal of Pharmacology, 157, 451-463 (Year: 2009).*
Tosun et al., Relationship Between Regional Brain Amyloid-beta Deposition and Brain Atrophy Rates in Mild Cognitive Impairment, 2010, Alzheimer's & Dementia, vol. 6, Issue 4, p. e15 (Year: 2010).*

(Continued)

*Primary Examiner* — Kristin A Vajda
(74) *Attorney, Agent, or Firm* — Sughrue Mion, PLLC

(57) ABSTRACT

An object of the present invention is to provide a drug which prevents progress of Alzheimer's disease and a method of preventing progress of Alzheimer's disease. 1-(3-(2-(1-benzothiophen-5-yl)ethoxy)propyl)azetidin-3-ol or a salt thereof has an effect of suppressing brain atrophy and is useful as an agent for preventing or treating brain atrophy. Brain atrophy observed in aging or neurodegenerative diseases can be prevented or treated by administering 1-(3-(2-(1-Benzothiophen-5-yl)ethoxy)propyl)azetidin-3-ol or a salt thereof.

8 Claims, 2 Drawing Sheets

(56) References Cited

FOREIGN PATENT DOCUMENTS

| JP | 2012-523437 A | 10/2012 |
|---|---|---|
| JP | 2012-526821 A | 11/2012 |
| KR | 10-2008-0111131 A | 12/2008 |
| RU | 2496784 C2 | 10/2013 |
| RU | 2015112914 A | 11/2016 |
| WO | 99/11293 A1 | 3/1999 |
| WO | 03/035647 A1 | 5/2003 |
| WO | 03/105830 A1 | 12/2003 |
| WO | 2007/125913 A1 | 11/2007 |
| WO | 2011/057199 A1 | 5/2011 |
| WO | 2013/125617 A1 | 8/2013 |
| WO | 2015/115582 A1 | 8/2015 |
| WO | 2015/191506 A2 | 12/2015 |
| WO | 2016/051799 A1 | 4/2016 |
| WO | 2016/124508 A1 | 8/2016 |
| WO | 2016/199878 A1 | 12/2016 |
| WO | 2017/111005 A1 | 6/2017 |

OTHER PUBLICATIONS

Office Action dated Jun. 10, 2021 in U.S. Appl. No. 16/617,660.
Sarva et al., "Treatment Options in Degenerative Cerebellar Ataxia: A Systematic Review", Movement Disorders Clinical Practice, 2014, vol. 1, pp. 291-298.
Horig et al., "From bench to clinic and back: Perspective on the 1st IQPC Translational Research conference", Journal of Translational Medicine, 2004, vol. 2, No. 44, pp. 1-8.
Schafer et al., "Failure is an option: learning from unsuccessful proof-of concept trials", Drug Discovery Today, 2008, vol. 13, pp. 913-916.
Decision under section 15 dated Mar. 22, 2021 issued in subject matter-related Indian patent application No. 201947049392.
Decision under section 15 dated Mar. 22, 2021 issued in subject matter-related Indian patent application No. 201947049390.
Office Action dated Jun. 1, 2021 issued in corresponding Singapore patent application No. 11201911512S.
Office Action dated Jun. 1, 2021 issued in subject matter-related Singapore patent application No. 11201911515Q.
Office Action dated Jun. 1, 2021 issued in subject matter-related Singapore patent application No. 11201911520U.
Office Action dated Jun. 1, 2021 issued in subject matter-related Singapore patent application No. 11201911519U.
Mascalchi et al., "Progression of Brain Atrophy in Spinocerebellar Ataxia Type 2: A Longitudinal Tensor-Based Morphometry Study", PLOS One, 2014, vol. 9, Issue 2, pp. 1-7, e89410.
Tosun et al., "Spatial patterns of brain amyloid-β burden and atrophy rate associations in mild cognitive impairment", Brain, 2011, vol. 134, pp. 1077-1088.
Office Action dated Sep. 25, 2020 in Russian Application No. 2019138166.
Office Action dated Oct. 23, 2020 in Russian Application No. 2019138538, corresponding to U.S. Appl. No. 16/617,607.
Kolobov et al., "Modern Pharmacological Models of Alzheimer's Disease", Original Articles, Experimental Neurology, 2014, vol. 8, No. 3, pp. 38-44 (32 pages total).
Grimmer et al., "Beta Amyloid in Alzheimer's Disease: Increased Deposition in Brain is Reflected in Reduced Concentration in Cerebrospinal Fluid", Biol. Psychiatry, 2009, vol. 65, No. 11, pp. 927-934 (17 pages total).
Office Action dated May 26, 2020 in Indian Application No. 201947049400.
Office Action dated Mar. 2, 2020 in Russian Application No. 2019138164, corresponding to U.S. Appl. No. 16/617,660.
Extended European Search Report dated May 11, 2020 in European Application No. 18809579.8, corresponding to U.S. Appl. No. 16/617,552.
Extended European Search Report dated May 11, 2020 in European Application No. 18809739.8, corresponding to U.S. Appl. No. 16/617,660.
Extended European Search Report dated May 13, 2020 in European Application No. 18809110.2 corresponding to U.S. Appl. No. 16/617,607.
Office Action dated May 26, 2020 in Indian Application No. 201947049390, corresponding to U.S. Appl. No. 16/617,607.
Office Action dated May 26, 2020 in Indian Application No. 201947049392, corresponding to U.S. Appl. No. 16/617,660.
Office Action dated May 26, 2020 in Indian Application No. 201947049401, corresponding to U.S. Appl. No. 16/617,739.
Kawasaki et al., "A Neuroprotective Agent, T-817MA (1-{3-[2-(1-benzothiophen-5-yl)ethoxy]propyl}azetidin-3-ol Maleate), Prevents 1-methyl-4-phenyl-1,2,3,6-tetrahydropyridine-induced Neurotoxicity in Mice", Neuropharmacology, vol. 55, Issue 5, Oct. 2008, pp. 654-660, Abstract only.
Office Action dated Dec. 8, 2020, issued by the Korean Intellectual Property Office in Korean Application No. 10-2019-7035347, corresponding to U.S. Appl. No. 16/617,739 (the present application).
Office Action dated Dec. 9, 2020, issued by the Korean Intellectual Property Office in Korean Application No. 10-2019-7035350, corresponding to U.S. Appl. No. 16/617,607.
Office Action dated Dec. 8, 2020, issued by the Korean Intellectual Property Office in Korean Application No. 10-2019-7035348, corresponding to U.S. Appl. No. 16/617,660.
Office Action dated Dec. 9, 2020, issued by the Korean Intellectual Property Office in Korean Application No. 10-2019-7035349, corresponding to U.S. Appl. No. 16/617,552.
Hearing Notice dated Jan. 8, 2021, issued by the Indian Intellectual Property Office in Indian Application No. 201947049401, corresponding to U.S. Appl. No. 16/617,739 (the present application).
Hearing Notice dated Feb. 3, 2021 issued by the Indian Patent Office in Application No. 201947049390, corresponding to U.S. Appl. No. 16/617,607.
Hearing Notice dated Feb. 3, 2021 issued by the Indian Patent Office in Application No. 201947049400, corresponding to U.S. Appl. No. 16/617,552.
Official Action dated Jan. 27, 2021 issued by the Canadian Patent Office in Application No. 3,067,453, corresponding to U.S. Appl. No. 16/617,739 (the present application).
Office Action dated Jan. 27, 2021 issued by the Canadian Patent Office in Application No. 3,067,455, corresponding to U.S. Appl. No. 16/617,660.
Official Action dated Jan. 27, 2021 issued by the Canadian Patent Office in Application No. 3,067,456, corresponding to U.S. Appl. No. 16/617,552.
Official Action dated Jan. 29, 2021 issued by the Canadian Patent Office in Application No. 3,067,458, corresponding to U.S. Appl. No. 16/617,607.
Hearing Notice dated Jan. 8, 2021 issued by the Indian Patent Office in application No. 201947049392, corresponding to U.S. Appl. No. 16/617,660.
Office Action dated Aug. 10, 2020 in Australian Application No. 2018276638, subject matter-related to U.S. Appl. No. 16/617,552.
Office Action dated Aug. 14, 2020 in Australian Application No. 2018277981, subject matter-related to U.S. Appl. No. 16/617,552.
Office Action dated Aug. 17, 2020 in Australian Application No. 2018277983, subject matter-related to U.S. Appl. No. 16/617,552.
Office Action dated Aug. 21, 2020 in Australian Application No. 2018277982, subject matter-related to U.S. Appl. No. 16/617,552.
Office Action dated Jul. 3, 2020 in Russian Application No. 2019138699, corresponding to U.S. Appl. No. 16/617,552.
Office Action dated May 29, 2020 in Russian Application No. 2019138538, corresponding to U.S. Appl. No. 16/617,607.
Hirata et al., "A Novel Neurotrophic Agent, T-817MA [1-{3-[2-(1-Benzothiopen-5-yl) Ethoxy] Propyl}-3-azetidinol Maleate], Attenuates Amyloid-β-Induced Neurotoxicity and Promotes Neurite Outgrowth in Rat Cultured Central Nervous System Neurons", The Journal of Pharmacology and Experimental Therapeutics, vol. 314, No. 1, pp. 252-259, 2005 (8 pages total).
Uehara et al., "T-817MA, a novel neurotrophic agent, ameliorates loss of GABAergic parvalbumin-positive neurons and sensorimotor gating deficits in rats transiently exposed to MK-801 in the neonatal period", Journal of Psychiatric Research, vol. 46, No. 5, pp. 622-629, 2012 (8 pages total).

(56) References Cited

OTHER PUBLICATIONS

Decision under section 15 dated Feb. 23, 2021, issued in corresponding Indian Application No. 201947049401.
Office Action dated Feb. 17, 2021, issued in corresponding Russian Application No. 2019138166/04.
Tosun et al., "Relationship Between Regional Brain Amyloid-β Deposition and Brain Atrophy Rates in Mild Cognitive Impairment", Alzheimer's & Dementia: The Journal of the Alzheimer's Association, Jul. 1, 2010, XP027440489, vol. 6, No. 4, p. e15 (total 1 page).
Extended European Search Report dated May 7, 2020 from European Patent Office in EP Application No. 18810520.9, corresponding to the present application.
Schneider et al., "A Phase 2 Multicenter, Randomized, Placebo-Controlled Trial to Evaluate the Efficacy and Safety of Edonerpic (T-817) In Patients with Mild to Moderate Alzheimer's Disease", Alzheimer's & Dementia: The journal of the Alzheimer's Association, Jul. 19, 2017, P4-573. vol. 13, No. 7, XP085218926, p. P1572 (total 1 page).
Yamaguchi et al., "T-817MA, a neurotrophic compound, reverses Aβ neurotoxicity and promotes neurite outgrowth through PI3-Kinase pathway in rat primary neurons", Abstract of the Annual Meeting of the Society for Neuroscience, Nov. 8, 2003, XP008135922, pp. 1-2 (total 2 pages).
Quinti et al., "A Novel Drug-Screening Platform in Microglial Cells Indentifies Potential AD Drugs", Alzheimer's & Dementia: The journal of the Alzheimer's Association, Jul. 19, 2017, XP085218817, P4-404, vol. 1, No. 13, p. P1485 (total 1 page).
Yano et al., "SIGMA-1 Receptor is a Molecular Target for Novel Neuropretectant T-817MA", Alzheimer's & Dementia: The Journal of the Alzheimer's Association, Jul. 1, 2015, XP029355158, P4-210, vol. 11, No. 7, p. P861 (total 1 page).
Nakagawa et al., "T-817MA, A Newly Developing Anti-Alzheimer's Agent, Protects Neurons and Recovers Memory Impairment in Amyloid B-Infused Rats and P301L Taumutated Mice", Alzheimer's & Dementia: The Journal of the Alzheimer's Association, Jul. 1, 2005, XP027823394, P-193, vol. 1, No. 1, p. S69-S70 (total 2 pages).
Extended European Search Report dated May 11, 2020 from European Patent Office in EP Application No. 18810759.3, corresponding to U.S. Appl. No. 16/617,584.
Office Action dated Apr. 27, 2020 from the Russian Patent Office in Russian Application No. 2019138166/04.
U.S. Appl. No. 16/617,660, Hiroshi Kobayashi, et al., filed Nov. 27, 2019, Pending.
International Search Report dated Jul. 24, 2018 in International Application No. PCT/JP2018/021225, corresponding to U.S. Appl. No. 16/617,552.
Written Opinion dated Jul. 24, 2018 in International Application No. PCT/JP2018/021225, corresponding to U.S. Appl. No. 16/617,552.
International Search Report dated Sep. 4, 2018 in International Application No. PCT/JP2018/021222, corresponding to U.S. Appl. No. 16/617,584.
Written Opinion dated Sep. 4, 2018 in International Application No. PCT/JP2018/021222, corresponding to U.S. Appl. No. 16/617,584.
International Search Report dated Jul. 24, 2018 in corresponding International Application No. PCT/JP2018/021223.
Written Opinion dated Jul. 24, 2018 in corresponding International Application No. PCT/JP2018/021223.
International Search Report dated Jul. 24, 2018 in International Application No. PCT/JP2018/021224, corresponding to U.S. Appl. No. 16/617,660.
Written Opinion dated Jul. 24, 2018 in International Application No. PCT/JP2018/021224, corresponding to U.S. Appl. No. 16/617,660.
International Search Report dated Jul. 24, 2018 in International Application No. PCT/JP2018/021226, corresponding to U.S. Appl. No. 16/617,607.
Written Opinion dated Jul. 24, 2018 in International Application No. PCT/JP2018/021226, corresponding to U.S. Appl. No. 16/617,607.
International Preliminary Report on Patentablity dated Dec. 3, 2019 in International Application No. PCT/JP2018/021222, corresponding to U.S. Appl. No. 16/617,584.
International Preliminary Report on Patentablity dated Dec. 3, 2019 in corresponding International Application No. PCT/JP2018/021223.
International Preliminary Report on Patentablity dated Dec. 3, 2019 in International Application No. PCT/JP2018/021224, corresponding to U.S. Appl. No. 16/617,660.
International Preliminary Report on Patentablity dated Dec. 3, 2019 in International Application No. PCT/JP2018/021225, corresponding to U.S. Appl. No. 16/617,552.
International Preliminary Report on Patentablity dated Dec. 3, 2019 in International Application No. PCT/JP2018/021226, corresponding to U.S. Appl. No. 16/617,607.
"2012 Alzheimer's Disease Facts and Figures", Alzheimer's Association, 2012 (72 pages total); http://www.alz.org/downloads/facts_figures_2012.pdf.
Sugimoto, "Development of Anti-Alzheimer's Disease Drug Based on Beta-Amyloid Hypothesis", Yakugaku Zasshi, 2010, vol. 130, No. 4, pp. 521-526 (6 pages total).
"Epidemiological studies on Alzheimer's disease in Japan", Japanese Journal of Clinical Medicine, 2008, vol. 66 (Extra ed. 1), pp. 23-27 (5 pages total).
Press Release by Seed Planning (Dec. 28, 2010) (3 pages total); http://www.seedplanning.co.jp/press/2010/2010122801.html.
Japanese Journal of Clinical Psychopharmacology, 2011, vol. 14, No. 7, pp. 1123-1129.
Japanese Journal of Clinical Psychopharmacology, 2012, vol. 15, No. 3, pp. 311-321.
Takamura et al., "Effects of the neurotrophic agent T-817MA on oligomeric amyloid-β-induced deficits in long-term potentiation in the hippocampal CA1 subfield", Neurobiology of Aging, 2014, vol. 35, pp. 532-536 (5 pages total).
Fujifilm Corp., "II stage clinical experiment in the United States for Alzheimer's dementia therapeutic drug 'T-817MA': drastically restricting, with statistical significant difference, progress of deterioration in cognitive function with respect to patient group having this innovative two effects of reducing phosphorylation tau in cerebrospinal fluid and restricting hippocampal atrophy in brain", News release, Jul. 19, 2017 (1 page total).
McKhann et al., "The diagnosis of dementia due to Alzheimer's disease: Recommendations from the National Institute on Aging-Alzheimer's Association workgroups on diagnostic guidelines for Alzheimer's disease", Alzheimer's Dement., May 2011, vol. 7, No. 3, pp. 263-269, (52 pages total).
Kimura et al., "T-817MA, a neurotrophic agent, ameliorates the deficits in adult neurogenesis and spatial memory in rats infused i.c.v. with amyloid-β peptide", British Journal of Pharmacology, 2009, vol. 157, pp. 451-463 (13 pages total).
Moreno et al., "Blocking effects of human tau on squid giant synapse transmission and its prevention by T-817MA", Frontiers in Synaptic Neuroscience, May 2011, vol. 3, Article 3, pp. 1-8 (8 pages total).
Fukushima et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734 (5 pages total).
Fukushima, "Pharmacological properties of T-817MA, a novel neurotrophic agent, for treatment of Alzheimer's disease", Folia Pharmacologica Japonica, 2010, vol. 136, pp. 11-14 (2 pages total).
Proceedings of the Annual Meeting of the Japanese Research Group on Senile Dementia, 2010, vol. 15, pp. 79-81 (4 pages total).
Lo et al., "Longitudinal Change of Biomarkers in Cognitive Decline", Archives of Neurology, 2011, vol. 68, No. 10, pp. 1257-1266 (10 pages total).
Japanese Journal of Geriatrics, 2013, vol. 50, No. 1, pp. 1-8 (9 pages total).
Jack Jr. et al., "Tracking pathophysiological processes in Alzheimer's disease: an updated hypothetical model of dynamic biomarkers", Lancet Neurology, Feb. 2013, vol. 12, No. 2, pp. 207-216 (10 pages total).

(56) References Cited

OTHER PUBLICATIONS

Office Action dated Aug. 19, 2021 in U.S. Appl. No. 16/617,584.
Shigemori et al., "The factorial structure of the mini mental state examination (MMSE) in Japanese dementia patients", BMC Geriatrics, 2010, vol. 10, Issue 36, pp. 1-7.
Colovic et al., "Acetylcholinesterase inhibitors: Pharmacology and Toxicology", Current Neuropharmacology, 2013, vol. 11, pp. 315-335.
Office Action dated Jun. 23, 2021 in U.S. Appl. No. 16/617,607.
Nguyen et al., "Ameliorative Effects of a Neuroprotective Agent, T-817MA, on Place Learning Deficits Induced by Continuous Infusion of Amyloid-β Peptide (1-40) in Rats", Hippocampus, 2007, vol. 17, pp. 443-455.
Office Action dated Jul. 21, 2021 in New Zealand Application No. 759647, corresponds to U.S. Appl. No. 16/617,660.
Office Action dated Jul. 21, 2021 in New Zealand Application No. 759657, corresponds to U.S. Appl. No. 16/617,552.
Office Action dated Jul. 22, 2021 in New Zealand Application No. 759662, corresponds to U.S. Appl. No. 16/617,607.
Office Action dated Nov. 9, 2021 in U.S. Appl. No. 16/617,607.
Restriction Requirement dated Jun. 3, 2021 in U.S. Appl. No. 16/760,512.
Office Action dated Aug. 18, 2021 in U.S. Appl. No. 16/760,512.
Marquer et al., "Increasing membrane cholesterol of neurons in culture recapitulates Alzheimer's disease early phenotypes", Molecular Neurodegeneration, 2014, vol. 9, No. 60, pp. 1-13 (13 pages total).
Chemical Abstracts Registry No. 519187-30-5, Indexed in the Registry file on STN CAS Online, May 23, 2003 (1 page total).
Bae et al., "Cholesterol biosynthesis from lanosterol: molecular cloning, chromosomal localization, functional expression and liver-specific gene regulation of rat sterol $\Delta^8$-isomerase, a cholesterogenic enzyme with multiple functions", Biochem. J., 2001, vol. 353, pp. 689-699 (11 pages total).
Berardi et al., "Novel 4-(4-Aryl)cyclohexyl-1-(2-pyridyl)piperazines as $\Delta_8$-$\Delta_7$ Sterol Isomerase (Emopamil Binding Protein) Selective Ligands with Antiproliferative Activity", J. Med. Chem., 2008, vol. 51, No. 23, pp. 7523-7531 (9 pages total).
Communication dated Jul. 3, 2020, from the European Patent Office in application No. 18873445.3, corresponds to U.S. Appl. No. 16/760,512.
Derry et al., "Mutations in a $\Delta^{8-\Delta 7}$ sterol isomerase in the tattered mouse and X-linked dominant chondrodysplasia punctata", Nature Genetics, Jul. 1999, vol. 22, pp. 286-290 (5 pages total).
International Preliminary Report on Patentability dated May 5, 2020, issued by the International Bureau in application No. PCT/JP2018/040283, corresponds to U.S. Appl. No. 16/760,512.
International Search Report dated Jan. 29, 2019, issued by the International Searching Authority in application No. PCT/JP2018/040283, corresponds to U.S. Appl. No. 16/760,512.
Laggner et al., "Discovery of High-Affinity Ligands of $\sigma_1$ Receptor, ERG2, and Emopamil Binding Protein by Pharmacophore Modeling and Virtual Screening", J. Med. Chem., 2005, vol. 48, No. 15, pp. 4754-4764 (11 pages total).
Moebius et al., "Identification of a 27-kDa High Affinity Phenylalkylamine-Binding Polypeptide as the $\sigma_1$ Binding Site by Photoaffinity Labeling and Ligand-Directed Antibodies", Molecular Pharmacology, 1993, vol. 44, pp. 966-971 (8 pages total).
Silve et al., "Emopamil-binding Protein, a Mammalian Protein That Binds a Series of Structurally Diverse Neuroprotective Agents, Exhibits $\Delta 8$-$\Delta 7$ Sterol Isomerase Activity in Yeast", The Journal of Biological Chemistry, Sep. 13, 1996, vol. 271, No. 37, pp. 22434-22440 (8 pages total).
Written Opinion dated Jan. 29, 2019, issued by the International Searching Authority in application No. PCT/JP2018/040283, corresponds to U.S. Appl. No. 16/760,512.
Office Action dated Nov. 4, 2021 in Mexican Application No. MX/a/2019/014306, corresponds to U.S. Appl. No. 16/617,607.
Office Action dated Jul. 21, 2021 in New Zealand Application No. 759585.

U.S. Appl. No. 16/617,584, Hiroshi Kobayashi, et al., filed Nov. 27, 2019, Pending.
U.S. Appl. No. 16/617,660, Hiroshi Kobayashi, et al., filed Nov. 27, 2019, Allowed.
U.S. Appl. No. 16/617,552, Hiroshi Kobayashi, et al., filed Nov. 27, 2019, Pending.
U.S. Appl. No. 16/617,607, Hiroshi Kobayashi, et al., filed Nov. 27, 2019, Pending.
U.S. Appl. No. 16/760,512, Takeaki Yano, et al., filed Apr. 30, 2020, Pending.
Office Action dated Jun. 25, 2021 in Korean Application No. 10-2019-7035347.
Office Action dated Jul. 2, 2021 in U.S. Appl. No. 16/617,552.
Blennow, "Cerebrospinal Fluid Protein Biomarkers for Alzheimer's Disease", The American Society for Experimental NeuroTherapeutics, Apr. 2004, vol. 1, pp. 213-225 (13 pages total).
Office Action dated Jun. 10, 2021 in Russian Application No. 2019138538, corresponds to U.S. Appl. No. 16/617,607.
Grigorenko et al., "Molecular Basics of Alzheimer's Disease", Molekulyarnaya Biologiya, 2007, vol. 41, No. 2, pp. 331-345 (15 pages total).
Lemere et al., "Sequence of Deposition of Heterogeneous Amyloid β-Peptides and APO E in Down Syndrome: Implications for Initial Events in Amyloid Plaque Formation", Neurobiology of Disease, 1996, vol. 3, No. 1, pp. 16-32, Article No. 0003 (17 pages total).
Office Action dated Jun. 10, 2021 in Mexican Application No. MX/a/2019/014306, corresponds to U.S. Appl. No. 16/617,607.
Office Action dated Jun. 24, 2021 in Korean Application No. 10-2019-7035349, corresponds to U.S. Appl. No. 16/617,552.
Office Action dated Jun. 24, 2021 in Korean Application No. 10-2019-7035350, corresponds to U.S. Appl. No. 16/617,607.
Office Action dated Jun. 25, 2021 in Korean Application No. 10-2019-7035348, corresponds to U.S. Appl. No. 16/617,660.
Manto et al., "Animal Models of Human Cerebellar Ataxias: a Cornerstone for the Therapies of the Twenty-First Century", Cerebellum, 2009, vol. 8, pp. 137-154 (18 pages total).
Office Action dated Jul. 13, 2021 in Japanese Application No. 2019-521350, corresponds to U.S. Appl. No. 16/617,552.
Shimohama et al., Journal of Japan Senile Medicine, vol. 50, No. 1, pp. 50:1-50:8, 2013 (8 pages total).
Notice of Allowance dated Sep. 28, 2021 in U.S. Appl. No. 16/617,660.
Communication dated Aug. 4, 2021 from the Canadian Patent Office in Canadian Application No. 3,067,456, corresponds to U.S. Appl. No. 16/617,552.
Communication dated Aug. 11, 2021 from the Canadian Patent Office in Canadian Application No. 3,067,458, corresponds to U.S. Appl. No. 16/617,607.
Communication dated Aug. 17, 2021 from the Mexican Patent Office in Mexican Application No. MX/a/2019/014306, corresponds to U.S. Appl. No. 16/617,607.
Notice of Final Rejection dated Aug. 24, 2021 by the Korean Patent Office in Korean Application No. 10-2019-7035348, corresponds to U.S. Appl. No. 16/617,660.
SIM Integrated Internal Medicine understood through anatomy and pathophysiology 10: Neurology Spinocerebellar Degeneration, May 30, 2013 (12 pages total).
Office Action dated Dec. 20, 2021 in corresponding Korean Application No. 10-2019-7035347.
Chetelat et al., "Relationship between Atrophy and β-Amyloid Deposition in Alzheimer Disease", Ann Neurol, 2010, vol. 67, pp. 317-324 (8 pages total).
Aisen et al., "On the path to 2025: understanding the Alzheimer's disease continuum", Alzheimer's Research & Therapy, 2017, vol. 9, No. 60, pp. 1-10 (10 pages total).
Head et al., "Alzheimer's Disease in Down Syndrome", Eur J Neurodegener Dis., 2012, vol. 1, No. 3, pp. 353-364 (16 pages total).
Office Action dated Feb. 14, 2022 in U.S. Appl. No. 16/617,607.
Office Action dated Jan. 25, 2022 in Russian Application No. 2019138538, corresponds to U.S. Appl. No. 16/617,607.
Office Action dated Jan. 28, 2022 in U.S. Appl. No. 16/617,552.

(56) References Cited

OTHER PUBLICATIONS

Decision of Refusal dated Nov. 30, 2021 from the Japanese Patent Office in Japanese Application No. 2019-521350, corresponds to U.S. Appl. No. 16/617,552.
A. Sugiyama and H. Shimada, "Tau PET Imaging for Dementia in Clinical Practice", Radioisotopes, vol. 65, No. 12, pp. 517-522 (Japan Radioisotope Association, 2016) (6 pages total).
Naoji Amano, "Neurodegenerative Diseases and Tauopathy", Shinshu Journal, 2002, vol. 50, No. 3, pp. 113-120 (8 pages total).
Y. Soeda and A. Takashima, "Development of disease modifying drugs for dementia—focusing on anti-tau drugs", Clinical Neurology, vol. 54, pp. 1178-1180 (2014) (3 pages total).
Y. Yoshiyama, Nippon Rinsho, Japanese Journal of Clinical Medicine, vol. 69, Suppl. 8, pp. 262-266 (2011) (5 pages total).
H. Takahashi, "Animal models of Alzheimer's disease for preclinical research", Folia Pharmacol. Jpn., vol. 136, No. 1, pp. 6-10 (2010) (5 pages total).
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Pharma and Toxicology, 2005, pp. 1-27 (30 pages total).
Final Office Action dated Dec. 8, 2021 in U.S. Appl. No. 16/760,512.
Office Action dated Dec. 14, 2021 in Korean Application No. 10-2019-7035349, corresponds to U.S. Appl. No. 16/617,552.
Office Action dated Dec. 14, 2021 in Korean Application No. 10-2019-7035350, corresponds to U.S. Appl. No. 16/617,607.
Busciglio et al., "Altered Metabolism of the Amyloid β Precursor Protein is Associated with Mitochondrial Dysfunction in Down's Syndrome", Neuron, 2002, vol. 33, pp. 677-688 (12 pages total).
Office Action dated Dec. 9, 2021 in Mexican Application No. MX/a/2019/014300, corresponding to U.S. Appl. No. 16/617,552.
Notice of Allowance dated Dec. 15, 2021 in U.S. Appl. No. 16/617,660.
Office Action dated Mar. 3, 2022 in corresponding Mexican Application No. MX/a/2019/014310.
Notice of Allowance dated Mar. 14, 2022 in U.S. Appl. No. 16/617,584.
Office Action dated Feb. 18, 2022 in Canadian Application No. 3,067,456, corresponds to U.S. Appl. No. 16/617,552.
Office Action dated Mar. 2, 2022 in Mexican Application No. MX/a/2019/014302, corresponds to U.S. Appl. No. 16/617,660.
Office Action dated Mar. 1, 2022 in Mexican Application No. MX/a/2019/014306, corresponds to U.S. Appl. No. 16/617,607.
Notice of Allowance dated Apr. 4, 2022 in U.S. Appl. No. 16/617,607.
Office Action dated Apr. 4, 2022 in New Zealand Application No. 759662, corresponds to U.S. Appl. No. 16/617,607.
Office Action dated Mar. 31, 2022 in Korean Application No. 10-2019-703530, corresponds to U.S. Appl. No. 16/617,607.
Communication dated Apr. 7, 2022 from the Korean Patent Office in Korean Application No. 10-2019-7035349, corresponds to U.S. Appl. No. 16/617,552.
Communication dated Apr. 12, 2022 from the Korean Patent Office in Korean Application No. 10-2019-7035347.
Office Action dated May 6, 2022 in corresponding Chinese Application No. 201880035394.0.
Office Action dated May 10, 2022 in corresponding Japanese Application No. 2019-521348.
Peng Ying et al., "Progress of clinical trials in Alzheimer's disease drugs", Acta Pharmaceutica Sinica, 2016, vol. 51, No. 8, pp. 1185-1195 (11 pages total).
Office Action dated May 6, 2022 in Chinese Application No. 201880035501.X, corresponds to U.S. Appl. No. 16/617,660.
Office Action dated May 6, 2022 in Chinese Application No. 201880035503.9, corresponds to U.S. Appl. No. 16/617,552.
Office Action dated May 6, 2022 in Chinese Application No. 201880035521.7, corresponds to U.S. Appl. No. 16/617,607.
Office Action dated May 10, 2022 in Japanese Application No. 2019-521347, corresponds to U.S. Appl. No. 16/617,584.

Reconsideration Report by Examiner dated Apr. 28, 2022 in Japanese Application No. 2019-521350, corresponds to U.S. Appl. No. 16/617,552.
Yuli Xie, Pharmaceutical and Clinical Research, 2011, vol. 19, No. 1, pp. 1-7 (7 pages total).
Buccarello et al., "Sex Impact on Tau-Aggregation and Postsynaptic Protein Levels in the P301L Mouse Model of Tauopathy" Journal of Alzheimer's Disease, 2017, vol. 56, No. 4, pp. 1279-1292 (27 pages total).
Office Action dated May 24, 2022 in Japanese Application No. 2019-521349, corresponds to U.S. Appl. No. 16/617,660.
Office Action dated Jun. 6, 2022 in U.S. Appl. No. 16/617,552.
Office Action dated Jun. 7, 2022 in Japanese Application No. 2019-521351, corresponds to U.S. Appl. No. 16/617,607.
Zheng et al., "Amyloid β Peptide induces Tau Phosphorylation and Loss of Cholinergic Neurons in Rat Primary Septal Cultures", Neuroscience, 2002, vol. 115, No. 1, pp. 201-211 (11 pages total).
Office Action dated Apr. 12, 2022 in Israeli Application No. 270910, corresponds to U.S. Appl. No. 16/617,660.
Office Action dated Aug. 29, 2022 in Korean Application No. 10-2022-7022765, corresponds to U.S. Appl. No. 16/617,552.
Office Action dated Aug. 29, 2022 in Korean Application No. 10-2022-7022766, corresponds to U.S. Appl. No. 16/617,552.
Office Action dated Sep. 13, 2022 in Brazilian Application No. BR1120190248811, corresponds to U.S. Appl. No. 16/617,660.
Office Action dated Nov. 8, 2022 in Japanese Application No. 2019-521351, corresponds to U.S. Appl. No. 16/617,607.
Hanney et al., "Memantine for dementia in adults older than 40 years with Down's syndrome (Meadows): a randomised, double-blind, placebo-controlled, trial", Lancet, 2012, vol. 379, pp. 528-536 (9 pages total).
Livingstone et al., "Pharmacological interventions for cognitive decline in people with Down syndrome (Review)", Cochrane Database of Systematic Reviews, 2015, Issue 10, Art. No. CD011546 (57 pages total).
Office Action dated Jun. 27, 2022 in Israeli Application No. 270922, corresponds to U.S. Appl. No. 16/617,739 (the present application).
Office Action dated Oct. 18, 2022 in Japan Patent Office in Japanese Application No. 2019-550404, which corresponds to U.S. Appl. No. 16/760,512.
Office Action dated Jul. 26, 2022 in Brazilian Application No. BR1120190249834, corresponds to U.S. Appl. No. 16/617,607.
Office Action dated Aug. 16, 2022 in U.S. Appl. No. 16/617,607.
Notice of Allowance dated Aug. 15, 2022 in U.S. Appl. No. 16/617,584.
Office Action dated Jun. 26, 2022 in Israeli Application No. 270912, corresponds to U.S. Appl. No. 16/617,552.
Office Action dated Nov. 15, 2022 in Japanese Application No. 2019-521347, corresponds to U.S. Appl. No. 16/617,584.
Office Action dated Nov. 15, 2022 in Japanese Application No. 2019-521348, corresponds to U.S. Appl. No. 16/617,739.
Kimihiro Kimura et al., T-817MA ameliorates cognitive impairment in the Tg2576 transgenic mouse, Society for Neuroscience, Nov. 12-16, 2016.
Office Action dated Sep. 13, 2022 in Brazilian Application No. BR1120190248510.
Notice of Allowance dated Dec. 7, 2022 in U.S. Appl. No. 16/617,607.
Office Action dated Jan. 10, 2023 in U.S. Appl. No. 16/617,552.
Ramesh J. L. Kandimalla, et al., "CSF p-Tau levels in the prediction of Alzheimer's disease", Biology Open 2, 2013, pp. 1119-1124.
Official Action dated Jan. 5, 2023 issued in corresponding Singapore patent application No. 11201911512S.
Decision of Refusal dated Jan. 18, 2023 issued in corresponding Chinese patent application No. 201880035394.0.
Tatuso Kimura, et al., "T-817MA, a neurotrophic agent, ameliorates the deficits in adult neurogenesis and spatial memory in rats infused i.c.v. with amyloid-ßpeptide", British Journal of Pharmacology, 2009, vol. 157, pp. 451-463.
Yusaku Takamura, et al., "Effects of the neurotrophic agent T-817MA on oligomeric amyloid-ß-induced deficits in long-term potentiation in the hippocampal CA1 subfield", Neurobiology of Aging, 2014, vol. 35, pp. 532-536.

(56) References Cited

OTHER PUBLICATIONS

Herman Moreno, et al., "Blocking effects of human tau on squid giant synapse transmission and its prevention by T-817 MA", Frontiers in Synaptic Neuroscience, 2011, vol. 3, Article 3, 8 pages.
Tetsuo Fukushima, et al., "T-817MA, a neuroprotective agent, attenuates the motor and cognitve impairments associated with neuronal degeneration in P301L tau transgenic mice", Biochemical and Biophysical Research Communications, 2011, vol. 407, pp. 730-734.
Tetsuo Fukushima, "New regulation neurotrophic factor-like low molecular weight compound T817MA", 2010, 2 pages, Cited in Singapore Office Actions dated Jan. 5, 2023 in Application Nos. 11201911512S, 11201911515Q, 11201911520U, and 11201911519U.
Duygu Tosun, et al., "Spatial patterns of brain amyloid-βburden and atrophy rate associations in mild cognitive impairment", Brain A Journal of Neurology, 2011, vol. 134, pp. 1077-1088.
Official Action dated Jan. 5, 2023 issued in the related Singapore patent application No. 11201911515Q, corresponds to U.S. Appl. No. 16/617,660.
Official Action dated Jan. 5, 2023 issued in the related Singapore patent application No. 11201911520U, corresponds to U.S. Appl. No. 16/617,552.
Official Action dated Jan. 5, 2023 issued in the related Singapore patent application No. 11201911519U, corresponds to U.S. Appl. No. 16/617,607.
Official Action dated Jan. 18, 2023 issued in related Chinese patent application No. 201880035503.9, corresponds to U.S. Appl. No. 16/617,552.
Official Action dated Jan. 18, 2023 issued in the related Chinese patent application No. 201880035521.7, corresponds to U.S. Appl. No. 16/617,607.
Mario Mascalchi, et al., "Progression of Brain Atrophy in Spinocerebellar Ataxia Type 2: A Longitudinal Tensor-Based Morphometry Study", Plos One, Feb. 2014, vol. 9, Issue 2, e89410, 7 pages.
Masaya Nakagawa, et al., "T-817MA, A Newly Developing Anti-Alzheimer's Agent, Protects Neurons and Recovers Memory Impairment in Amyloid B-Infused Rats and P301L TAU-Mutated Mice", Abstracts: Pharmacological Treatments, 1 (Suppl 1), 2005, pp. S69-S70.
Preeti J. Khandelwal, et al., "Wild type and P301L mutant Tau promote neuro-inflammation and α-Synuclein accumulation in lentiviral gene delivery modles", Mol Cell Neurosci, Jan. 2012, vol. 49, No. 1; pp. 44-53 (22 pages).
W.-H Zheng, et al., "Amyloid βPeptide Induces TAU Phosphorylation and Loss of Cholinergic Neurons in Rat Primary Septal Cultures", Neuroscience, 2002, vol. 115, No. 1 pp. 201-211.
Ni-Chung Lee, et al., "Blood Beta-Amyloid and Tau in Down Syndrome: A Comparision with Alzheimer's Disease", Frontiers in Aging Neuroscience, Jan. 17, 2017, vol. 8, Article 316 (8 pages).
Official Action dated Jan. 5, 2023 issued in corresponding Singapore patent application No. 11201911512S.
Decision of Refusal dated Jan. 18, 2023 issued in corresponding Chinese patent application No. 201880035394.0.
Tatsuo Kimura, et al., "T-817MA, a neurotrophic agent, ameliorates the deficits in adult neurogenesis and spatial memory in rats infused i.c.v. with amyloid-βpeptide", British journal of Pharmacology, 2009, vol. 157, pp. 451-463.
Yusaku Takamura, et al., "Effects of the neurotrophic agent T-817MA on oligomeric amyloid-β-induced deficits in long-term potentiation in the hippocampal CA1 subfield", Neurobiology of Aging, 2014, vol. 35, pp. 532-536.
Herman Moreno, et al., "Blocking effects of human tau on squid giant synapse transmission and its prevention by T-817 MA", Frontiers in Synaptic Neuroscience, 2011, vol. 3, Article 3, 8 pages.
Tetsuo Fukushima, et al., "T-817MA, a neuroprotective agent, attenuates the motor and cognitve impairments associated with neuronal degeneration in P301L tau transgenic mice", Biochemical and Biophysical Research Communications, 2011, vol. 407, pp. 730-734.

Tetsuo Fukushims, "New regulation neurotrohic factor-like low molecular weight compound T817MA", 2010, 2 pages, Cited in Singapore Office Actions dated Jan. 5, 2023 in Application Nos. 11201911512S, 11201911515Q, 11201911520U, and 11201911519U.
Duygu Tosun, et al., "Spatial patterns of brain amyloid-βburden and atrophy rate associations in mild cognitive impairment", Brain A Journal of Neurology, 2011, vol. 134, pp. 1077-1088.
Official Action dated Jan. 5, 2023 issued in the related Singapore patent application No. 11201911515Q, corresponds to U.S. Appl. No. 16/617,660.
Official Action dated Jan. 5, 2023 issued in the related Singapore patent application No. 11201911520U, corresponds to U.S. Appl. No. 16/617,552.
Official Action dated Jan. 5, 2023 issued in the relaed Singapore patent application No. 11201911519U, corresponds to U.S. Appl. No. 16/617,607.
Official Action dated Jan. 18, 2023 issued in related Chinese patent application No. 201880035503.9, corresponds to U.S. Appl. no. 16/617,552.
Official Action dated Jan. 18, 2023 issued in the related Chinese patent application No. 201880035521.7, corresponds to U.S. Appl. No. 16/617,607.
Mario Mascalchi, et al., "Progression of Brain Atrophy in Spinocerebellar Ataxia Type 2: A Longitudinal Tensor-Based Morphometry Study", Plos One, Feb. 2014, vol. 9, Issue 2, e89410, 7 pages.
Masaya Nakagawa, et al., "T-817MA, A Newly Developing Anti-Alzheimer's Agent, Protects Neurons and Recovers Memory Impairment in Amyloid B-Infused Rats and P301L TAU-Mutated Mice", Abstracts: Pharmacological Treatments, 1 (Suppl 1), 2005, pp. S69-S70.
Preeti J. Khandelwal, et al., "Wild type and P301L mutant Tau promote neuro-inflammation and α- Synuclein accumulation in lentiviral gene delivery modles", Mol Cell Neurosci, Jan. 2012, vol. 49, No. 1; pp. 44-53 (22 pages).
W.-H. Zheng, et al., "Amyloid β Peptide Induces TAU Phosphorylation and Loss of Cholinergic Neurons in Rat Primary Septal Cultures", Neuroscience, 2002, vol. 115, No. 1, pp. 201-211.
Ni-Chung Lee, et al., "Blood Beta-Amyloid and Tau in Down Syndrome: A Comparison with Alzheimer's Disease", Frontiers in Aging Neuroscience, Jan. 17, 2017, vol. 8, Article 316 (8 pages).
Folia Pharmacologica Japonica, 2010, vol. 136, pp. 11-14 (5 pages), Cited in JPOA dated Mar. 7, 2023 in JP 2022-028810 and JPOA dated Mar. 7, 2023 in JP 2022-028811.
Mikio Shoji "Biomarker of Dementia: Contribution [to Diagnosis and Prediction]", Animus, 2014, No. 81, pp 17-26 (10 pages), Cited in JPOA dated Mar. 7, 2023 in JP 2022-028810.
Official Action dated Mar. 7, 2023 issued in Japanese patent application No. 2022-028810, corresponding to U.S. Appl. No. 16/617,552.
Official Action dated Mar. 7, 2023 issued in Japanese patent application No. 2022-028811, corresponding to U.S. Appl. No. 16/617,552.
Office Action dated Mar. 27, 2023 in Korean Application No. 10-2022-7022765, corresponding to U.S. Appl. No. 16/617,552.
Office Action dated Mar. 27, 2023 in Korean Application No. 10-2022-7022766, corresponding to U.S. Appl. No. 16/617,552.
"History of Changes for Study: NCT02079909: Efficacy and Safety of T-817MA in Patients with Mild to Moderate Alzheimers's Disease (US202)", ClinicalTrials.gov.archive, U.S. National Library of Medicine, May 16, 2017 (13 pages).
Office Action dated Sep. 23, 2023 in Chinese Application No. 201880035521.7, corresponding to U.S. Appl. No. 18/116,914.
Office Action dated Jun. 26, 2023 Israeli Application No. 270912, corresponding to U.S. Appl. No. 18/220,218.
Office Action dated Jun. 25, 2023 in Israeli Application No. 270922, corresponding to U.S. Appl. No. 16/617,739 ( the present application).
Office Action dated Jun. 30, 2023 by China National Intellectual Property Adminstration in Chinese Application No. 201880035521.7.
Chinese Action dated Jul. 1, 2023 by China National Intellectual Property Adminstration in Chinese Application No. 201880035503.9.

(56) References Cited

OTHER PUBLICATIONS

Chinese Office Action dated Jul. 1, 2023 in Chinese Application No. 201880035503.9, corresponding to U.S. Appl. No. 18/220,218.
Office Action dated Dec. 6, 2023 in U.S. Appl. No. 18/116,914.
Office Action dated Jan. 9, 2024 in Japanese Application No. 2023-021444, corresponding to U.S. Appl. No. 16/617,584.
Office Action dated Jan. 9, 2024 in Japanese Application No. 2023-021443.

* cited by examiner

[Figure 1]
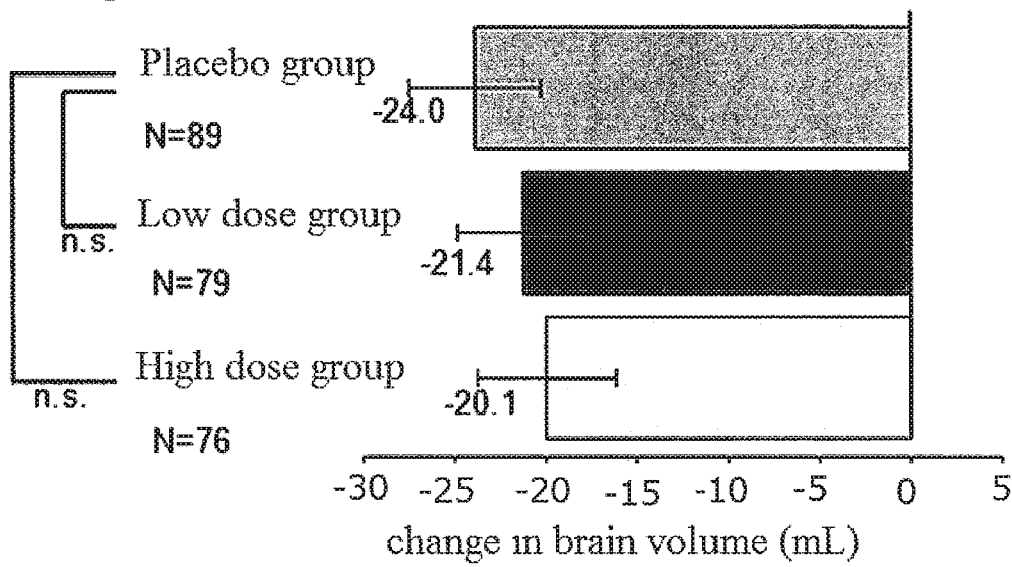
[Figure 2]
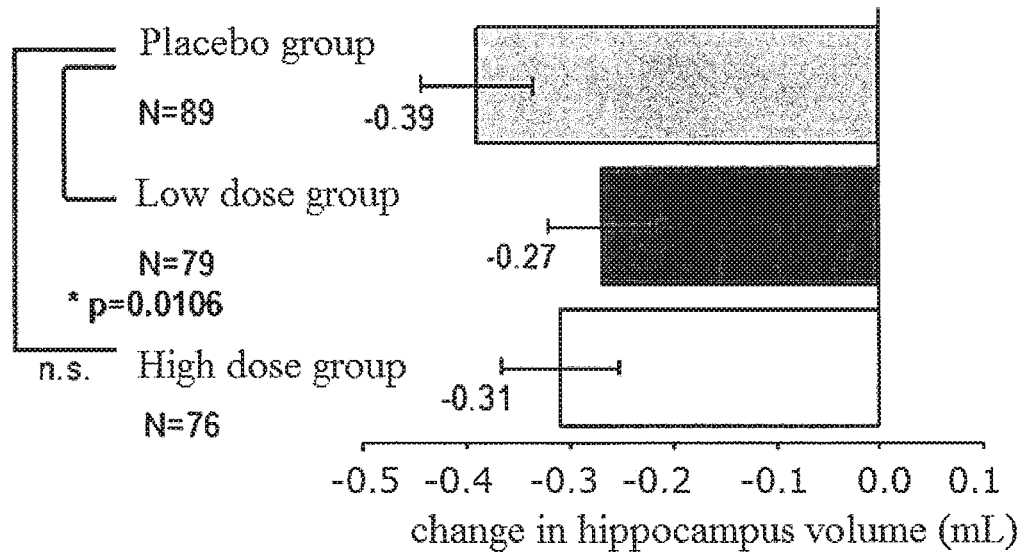

[Figure 3]
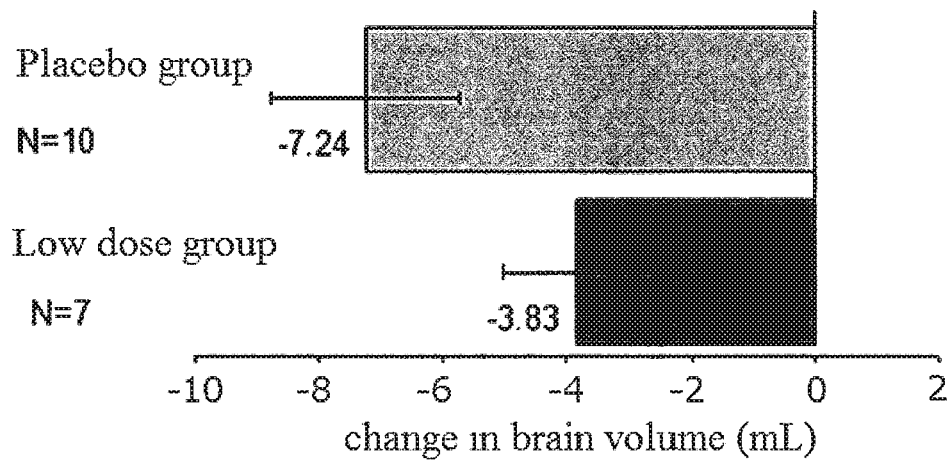
[Figure 4]
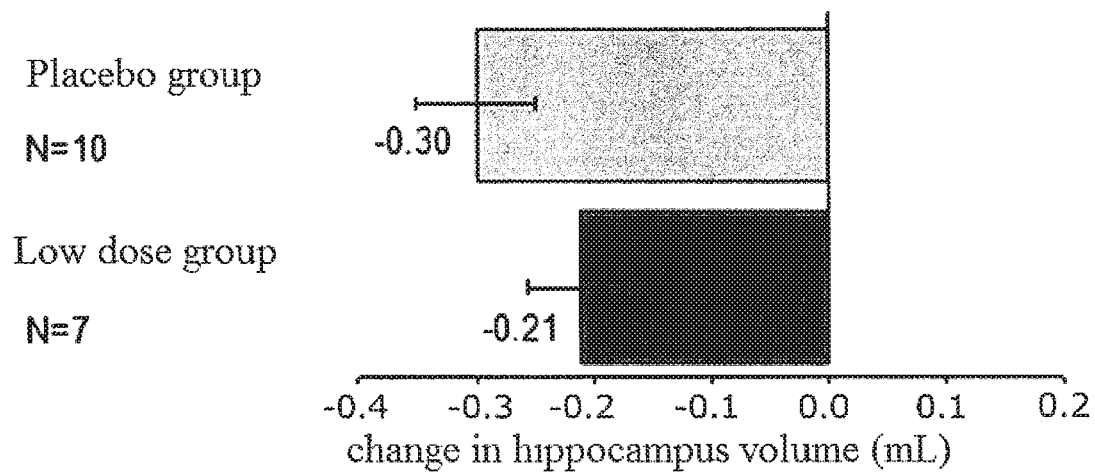

AGENT FOR PREVENTING OR TREATING BRAIN ATROPHY

CROSS REFERENCE TO RELATED APPLICATIONS

This application is a National Stage of International Application No. PCT/JP2018/021223 filed Jun. 1, 2018, claiming priority based on Japanese Patent Application No. 2017-109885 filed Jun. 2, 2017, Japanese Patent Application No. 2017-128472 filed Jun. 30, 2017 and Japanese Patent Application No. 2017-145100 filed Jul. 27, 2017.

TECHNICAL FIELD

The present invention relates to an agent for preventing or treating brain atrophy, comprising 1-(3-(2-(1-benzothiophen-5-yl)ethoxy)propyl)azetidin-3-ol or a salt thereof as an active ingredient.

BACKGROUND ART

Dementia is a neurodegenerative disease with significantly reduced cognitive function caused by, for example, brain atrophy and/or cerebrovascular disorder. Dementia is classified into some types by its cause, and 60% to 80% of the patients with dementia suffers from Alzheimer's disease (AD) (Non Patent Literature 1). The pathogenesis of AD is complicated, and the cause is considered to be the formation of senile plaques due to coagulation of amyloid-β protein (Aβ) or neurofibrillary changes caused by coagulation of phosphorylated Tau protein (p-Tau) (Non Patent Literature 2). The number of patients with AD in Japan is estimated to be about more than 1,160,000. The incidence is higher in advanced age, and thus with the aging of society, the number of patients is expected to increase rapidly, causing a greater burden on patients' family and a sharp rise in medical and nursing care expenses in the future (Non Patent Literatures 3, 4). Thus, treatment of AD is important for not only preventing patients' quality of life from decreasing and reducing burden on their family thereafter, but also reducing medical expenses in the future aging society.

Symptoms of dementia include core symptoms of cognitive impairment and peripheral symptoms such as problem behaviors seen when patients with cognitive impairment interact with people around them (Non Patent Literature 5). At present four agents are used as an agent for treating AD in Japan: donepezil hydrochloride, galantamine hydrobromide, and rivastigmine, which are acetylcholinesterase inhibitors, and memantine hydrochloride which is a N-methyl-D-aspartate receptor antagonist. These are all capable of reducing core symptoms or peripheral symptoms. However, these drugs are symptomatic drugs which improve core symptoms or peripheral symptoms for a certain period of time, and do not suppress neurodegeneration in AD. Although these drugs are temporally effective in improving cognitive function at the beginning of use, the cognitive function usually becomes worse than cognitive function before the treatment, after about 48 weeks or more (Non Patent Literature 6).

1-(3-(2-(1-benzothiophen-5-yl)ethoxy)propyl)azetidin-3-ol (hereinafter referred to as "Compound A") or a salt thereof is known to have neuroprotective, nerve regeneration-promoting and neurite outgrowth actions, and be useful as a therapeutic agent for central and peripheral neurological diseases (Patent Literature 1). Furthermore, a publication discloses that usually the drug may be administered to an adult in a dose or divided doses of 0.01 to 500 mg per day (Patent Literature 2).

PRIOR ART LITERATURES

Patent Literature

Patent Literature 1: International Publication No. WO 2003/035647
Patent Literature 2: International Publication No. WO 2003/105830

Non-Patent Literature

Non Patent Literature 1: 2012 Alzheimer's Disease Facts and Figures. (http://www.alz.org/downloads/facts_figures_2012.pdf)
Non Patent Literature 2: YAKUGAKU ZASSHI, 2010, Vol. 130, No. 4, pp. 521-526
Non Patent Literature 3: Japanese Journal of Clinical Medicine, 2008, Vol. 66 (Extra ed. 1), pp. 23-27
Non Patent Literature 4: Press Release by Seed Planning (Dec. 28, 2010) (http://www.seedplanning.co.jp/press/2010/2010122801.html)
Non Patent Literature 5: Japanese Journal of Clinical Psychopharmacology, 2011, Vol. 14, No. 7, pp. 1123-1129
Non Patent Literature 6: Japanese Journal of Clinical Psychopharmacology, 2012, Vol. 15, No. 3, pp. 311-321

SUMMARY OF INVENTION

Problem to be Solved by the Invention

Drugs which prevent progress of AD by inhibiting neurodegeneration need to be developed early. An object of the present invention is to provide a drug which prevents progress of AD and a method of preventing progress of AD.

Means for Solving Problem

In such circumstances, the present inventors have found that Compound A or a salt thereof has an effect of suppressing brain atrophy and have completed the present invention.

The present invention provides the following.

(1) An agent for preventing or treating brain atrophy, comprising Compound A or a salt thereof as an active ingredient.

(2) The agent for preventing or treating brain atrophy according to (1), wherein the agent is is orally administered in a dose of 100 mg to 400 mg in terms of Compound A once a day.

(3) The agent for preventing or treating brain atrophy according to (1), wherein the agent is orally administered in a dose of 160 mg or 320 mg in terms of Compound A once a day.

(4) The agent for preventing or treating brain atrophy according to any one of (1) to (3), wherein the agent is for administration to a patient with a neurodegenerative disease.

(5) The agent for preventing or treating brain atrophy according to any one of claims 1 to 3, wherein the agent is for administration to a patient with AD, Probable AD, Possible AD, Preclinical AD, Prodromal Alzheimer's disease, mild cognitive impairment due to Alzheimer's disease (MCI due to AD) or mild cognitive impairment (MCI).

(6) The agent for preventing or treating brain atrophy according to any one of (1) to (3), wherein the agent is for administration to a patient with AD, MCI due to AD or MCI.

(7) The agent for preventing or treating brain atrophy according to any one of (1) to (3), wherein the agent is for administration to a patient with AD.

(8) The agent for preventing or treating brain atrophy according to any one of (1) to (3), wherein the agent is for administration to a patient with MCI due to AD.

The present invention also provides the following.

(a) A pharmaceutical composition for preventing or treating brain atrophy, comprising Compound A or a salt thereof as an active ingredient.

(b) Compound A or a salt thereof for use in prevention or treatment of brain atrophy.

(c) A method of preventing or treating brain atrophy, comprising administering Compound A or a salt thereof to a patient.

(d) Use of Compound A or a salt thereof for producing an agent for preventing or treating brain atrophy.

(e) An agent for suppressing brain atrophy, comprising Compound A or a salt thereof as an active ingredient.

(f) Compound A or a salt thereof for use in suppression of brain atrophy.

(g) A method of suppressing brain atrophy, comprising administering Compound A or a salt thereof to a patient.

(h) Use of Compound A or a salt thereof for producing an agent for suppressing brain atrophy.

Advantageous Effects of Invention

Brain atrophy observed in aging or neurodegenerative diseases such as AD, progressive supranuclear palsy and frontotemporal dementia can be prevented or treated by administering Compound A or a salt thereof.

BRIEF DESCRIPTION OF DRAWINGS

FIG. 1 is a graph showing change in brain volume (the whole brain) at week 52 from that at screening in Test Example 1. "n.s." means that there was no statistically significant difference.

FIG. 2 is a graph showing change in brain volume (the hippocampus) at week 52 from that at screening in Test Example 1. "n.s." means that there was no statistically significant difference.

FIG. 3 is a graph showing change in brain volume (the whole brain) at week 52 from that at screening in Test Example 2.

FIG. 4 is a graph showing change in brain volume (the hippocampus) at week 52 from that at screening in Test Example 2.

EMBODIMENTS FOR CARRYING OUT THE INVENTION

Hereinafter the present invention will be described in detail.

In the present description, the respective terms have the following meaning unless otherwise specified.

In the present description, the numerical range shown with "to" represents a range inclusive of the value before and after "to" as the minimum and maximum value, respectively.

Compound A means 1-(3-(2-(1-benzothiophen-5-yl)ethoxy)propyl)azetidin-3-ol.

Examples of salts of Compound A include known salts of a basic group such as amino group or an acidic group such as hydroxyl group or carboxyl group.

Examples of salts of a basic group include salts with a mineral acid such as hydrochloric acid, hydrogen bromide, nitric acid and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with a sulfonic acid such as methanesulfonic acid, benzenesulfonic acid, p-toluenesulfonic acid, mesitylenesulfonic acid and naphthalenesulfonic acid.

Examples of salts of an acidic group include salts with an alkali metal such as sodium and potassium; salts with an alkaline earth metal such as calcium and magnesium; ammonium salts; and salts with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamin and N,N'-dibenzylethylenediamine.

Of the above salts, pharmacologically acceptable salts are preferred, and salts with maleic acid are more preferred.

In the case where Compound A or a salt thereof has isomers (e.g., optical isomers, geometric isomers and tautomers), the present invention includes all these isomers and also includes hydrates, solvates and any crystal forms thereof.

Prevention means to prevent the onset of a specific disease or at least one symptom caused by the disease.

Treatment means to reduce or improve at least one symptom caused by a specific disease with which a subject is affected, and delay the progress of the disease.

In an embodiment of the present invention, prevention means to inhibit or delay the onset or progress of brain atrophy in a patient with disease such as a neurodegenerative disease. Treatment means to inhibit or delay the progress of brain atrophy.

Mild to moderate Alzheimer's disease may be clinically diagnosed as "probable AD" according to the diagnosis criteria provided by the National Institute of Neurological and Communicative Disorders and Stroke/the Alzheimer's Disease and Related Disorders Associations (NINCDS-ADRDA).

A usual doctor may reasonably make clinical diagnosis of "mild to moderate Alzheimer's disease" using standard criteria. For example, according to the score of the standardized Mini-Mental State Examination (MMSE, scores of 0 to 30), clinical diagnosis of mild to moderate, moderate, or moderate to severe AD is provided. The MMSE (Folstein, Folstein and McHugh, 1975) is a simple test of cognitive function including an interview with patients. Orientation, memory, calculation and attention, language skills and other functions are assessed. The total score is 30. The lower the score, the higher the level of impairment of cognitive function.

In Test Examples of the present invention, patients with an MMSE score of 12 to 22 at the start of the test (screening) were determined as mild to moderate AD. Note that the MMSE is not the only way to clinically determine the grade of AD, though convenient.

Apolipoprotein E (ApoE), one of the apolipoproteins, constitutes lipoprotein and is involved in recognition of lipoprotein and lipid metabolism. ApoE has 3 isoforms of ApoE2, ApoE3 and ApoE4. A report shows that ApoE4 genotype encoding ApoE4 is correlated with the amount of deposition of amyloid-β protein in the brain and the ApoE4 genotype is a risk gene of Alzheimer's disease.

Structural change in the brain is observed is also observed in normal aging, and is accelerated by the development of neurodegenerative disease. In an embodiment of the present invention, examples of neurodegenerative disease include AD, Probable AD, Possible AD, Preclinical AD, Prodromal AD, MCI due to AD, MCI, progressive supranuclear palsy and frontotemporal dementia; preferably AD, Probable AD, Possible AD, Preclinical AD, Prodromal AD, MCI due to AD and MCI; more preferably AD and MCI due to AD and MCI; and further preferably AD and MCI due to AD. Diagnosis of Probable AD, Possible AD, Preclinical AD, Prodromal AD and MCI due to AD is described in Alzheimer's Dement., May 2011, Vol. 7, No. 3, pp. 263-292.

Brain atrophy in AD is caused by loss of neurons and synapses initiated in the entorhinal cortex. The lesion then spreads into the whole temporal limbic region including hippocampal formation, and neuronal loss and atrophy come to be seen all over the neocortical regions including the temporal lobe, the parietal lobe and the frontal lobe.

Volumetric MRI (vMRI) enables in vivo assessment of brain structure volume, offering scales of the rate of atrophy. Results of vMRI studies suggest that patterns of brain atrophy reflecting pathological progress of AD can be surely detected and monitored over time (Atiya et al. 2003). Atrophy of the medial temporal lobe including the hippocampus and the entorhinal cortex has long been reported in vMRI studies of AD (Jack et al. 1997). A vMRI-based hippocampal volume correlates with histologic hippocampal volume, neuronal loss and the level of AD (Jack et al. 2002). Change in the thickness of the entorhinal cortex is an early indicator of neurodegeneration associated with AD and is an index of susceptibility thereto. Longitudinal vMRI measurement of change in the regional and the whole brain volume complements cognitive assessment in that the measurement is not affected by temporary improvement of symptoms, and serves as an early indicator of the efficacy of drug for atrophy associated with AD.

Compound A or a salt thereof used in the present invention may be prepared by a method known per se or by combining such methods, or by the method disclosed in Patent Literature 1.

Compound A or a salt thereof used in the present invention may be blended with various pharmaceutical additives such as an excipient, a binding agent, a disintegrating agent, a disintegration inhibitor, a consolidation/adhesion-preventing agent, a lubricant, an absorption/adsorption carrier, a solvent, a bulking agent, an isotonic agent, a solubilizer, an emulsifier, a suspending agent, a thickener, a coating agent, an absorption enhancer, a gelling/procoagulant agent, a light stabilizer, a preservative, a desiccant, an emulsification/suspension/dispersion stabilizer, a color protecting agent, a deoxidant/antioxidant, a flavoring agent, a coloring agent, a foaming agent, an antifoaming agent, a soothing agent, an antistatic agent, a buffer, and/or a pH adjuster to give a pharmaceutical preparation such as an oral preparation (e.g., tablets, capsules, powders, granules, fine granules, pills, suspensions, emulsions, liquids, and syrups), injections, eye drops, nasal sprays and transdermal agents. Tablets are preferred as an oral dosage form for patients with AD.

The above agents are formulated by a usual method.

The method of administration of Compound A, which is not particularly limited, is accordingly determined based on the form of the preparation, the age, sex and other conditions of the patient and the level of symptoms of the patient.

The dose of Compound A is accordingly selected based on the administration, the age, sex, type of disease and other conditions of the patient.

The agent may be administered to an adult in a dose or divided doses of usually 40 to 500 mg in terms of Compound A per day. The agent is administered in a dose or divided doses of preferably 100 to 400 mg in terms of Compound A per day, and administered in a dose of further preferably 160 mg or 320 mg in terms of Compound A per day.

In the administration of Compound A or a salt thereof in the present invention, prevention or treatment by administration of acetylcholinesterase inhibitors (AChEIs) may also be included. Examples of AchEIs include donepezil hydrochloride, galantamine hydrochloride, rivastigmine tartrate and tacrine hydrochloride.

In the present invention, the subject may have undergone prevention or treatment by administration of AChEI for at least 6 months before administration of Compound A or a salt thereof.

Next, the present invention will be described with reference to Test Examples and Preparation Examples, but the present invention is not limited thereto.

Maleate of Compound A was used as the test compound.

Test Example 1

Multicenter Randomized Double-Blind Phase II Placebo-Controlled Trial for Assessing Effectiveness and Safety of Compound A in Mild to Moderate AD Patients Subject (selection criteria): Patients were screened in a period from 42 days before treatment assignment to the assignment based on the following selection criteria.

Patients who were probable AD and are 55 years old or older and 85 years old or younger at the time of obtaining consent of screening.

Patients with an MMSE score of 12 to 22 at the time of screening

Patients with a Modified Hachinski Ischemia Scale score of 4 or less

Patients who have been treated with a donepezil hydrochloride or rivastigmine transdermal system for at least 4 months before the baseline and with a stable dose thereof for 3 months before the baseline.

In the case of patients who have received memantine in addition to being treated with a donepezil hydrochloride or rivastigmine transdermal system, patients who have been treated with memantine for at least 4 months before the baseline and with a stable dose thereof for 3 months before the baseline.

Patients whose brain MRI or CT results match AD at the time of screening

Organization of groups: Patients matched (484 patients) were randomly divided into the following 3 groups and the trial was started.

(1) High dose group: 224 mg of a test compound (160 mg in terms of Compound A) was orally administered once a day for 4 weeks and then 448 mg of a test compound (320 mg in terms of Compound A) was orally administered once a day for 48 weeks (158 patients)

(2) Low dose group: 224 mg of a test compound (160 mg in terms of Compound A) was orally administered once a day for 52 weeks (166 patients)

(3) Placebo group: placebo was orally administered once a day for 52 weeks (158 patients)

Method of Assessment:
Volumetric MRI

Brain volume of subjects was measured by vMRI scan at the screening and after 52 weeks, and the volume change of the whole brain and the hippocampus of the subjects were quantified to assess brain atrophy based on the change from the screening.

Furthermore, volume change of the whole brain and 101 areas (obtained by dividing the areas existing in both the left brain and the right brain of the Brodmann areas (1 to 52) into 101 areas) in each subject was quantified to assess brain atrophy based on the change from the screening.

Statistical Analysis:

Changes in the volume of the whole brain and the hippocampus after 52 weeks from the baseline were compared between the high dose group and the placebo group, and between the low dose group and the placebo group based on Mixed-effect Models. For models, the treatment groups were included as a fixed effect, age, baseline of the respective brain volumes (the whole brain or the hippocampus), baseline of MMSE and ApoE4 genotype (positive/negative) were included as covariates, and trial sites were included as a random effect.

Furthermore, changes in the respective volumes of the whole brain and the 101 areas after 52 weeks from the baseline were compared between the high dose group and the placebo group, and between the low dose group and the placebo group.

Results: shown below

Change in brain volume obtained by vMRI scan at week 52 from the baseline is shown in Table 1, FIG. 1 and FIG. 2.

TABLE 1

| Group | Number of cases/statistics | Brain volume | |
|---|---|---|---|
| | | Whole brain (mL) | Hippocampus (mL) |
| High dose group | Number of cases | 76 | 76 |
| | Least square means (standard error) | −20.05 (3.821) | −0.31 (0.057) |
| | Difference from placebo group (95% Confidence interval) | 3.94 (−2.91, 10.79) | 0.08 (−0.02, 0.18) |
| | p-value | 0.2581 | 0.0996 |
| Low dose group | Number of cases | 79 | 79 |
| | Least square means (standard error) | −21.37 (3.582) | −0.27 (0.053) |
| | Difference from placebo group (95% Confidence interval) | 2.63 (−4.15, 9.40) | 0.12 (0.03, 0.22) |
| | p-value | 0.4456 | 0.0106 |
| Placebo group | Number of cases | 89 | 89 |
| | Least square means (standard error) | −23.99 (3.599) | −0.39 (0.054) |

For the change in the volume of the whole brain and the hippocampus at week 52 from the baseline, volume reduction tended to be smaller in the Compound A group than in the placebo group. The difference in effects on the change in hippocampal volume between the Compound A low dose group and the placebo group was statistically significant.

For change in brain volume obtained by vMRI scan at week 52 from the baseline, results for areas in which a statistically significant difference (p-value<0.05) was found in the comparison between the test compound low dose group and the placebo group are shown in Table 2.

TABLE 2

| | Placebo group | | Low dose group | | | |
|---|---|---|---|---|---|---|
| No. | Mean value | Variance | Mean value | Variance | p-value | Brain area |
| 1 | −2.0490 | 1.0716 | −0.9201 | 1.5655 | 0.0001 | Left-Cerebellum-White-Matter |
| 2 | −0.6899 | 0.7012 | −0.2695 | 0.6474 | 0.0005 | Left-Cerebellum-Cortex |
| 3 | −2.9861 | 1.4550 | −2.1332 | 1.4933 | 0.0013 | ctx-rh-superior temporal |
| 4 | −1.6919 | 1.3679 | −0.89 | 1.4082 | 0.0014 | Right-Cerebellum-White-Matter) |
| 5 | −2.6470 | 1.4373 | −1.9609 | 1.1486 | 0.0030 | ctx-lh-insula |
| 6 | −1.5952 | 0.5635 | −1.3142 | 0.5647 | 0.0054 | Whole brain |
| 7 | −2.6510 | 1.4746 | −1.9976 | 1.1656 | 0.0056 | ctx-rh-insula |
| 8 | −0.7248 | 0.8780 | −0.3209 | 0.8541 | 0.0090 | Right-Cerebellum-Cortex |
| 9 | −3.2601 | 1.4409 | −2.6157 | 1.4466 | 0.0124 | ctx-rh-inferior temporal) |
| 10 | −1.5322 | 1.4680 | −0.8995 | 1.4382 | 0.0146 | ctx-rh-lateral orbitofrontal |
| 11 | −1.4416 | 0.8598 | −1.0753 | 0.8417 | 0.0157 | Right-Cerebral-White-Matte) |
| 12 | −3.8173 | 2.1618 | −2.97 | 1.9228 | 0.0195 | ctx-lh-entorhinal |
| 13 | −1.5679 | 0.8570 | −1.2418 | 0.7405 | 0.0215 | Left-Cerebral-White-Matter |
| 14 | −3.0880 | 1.7450 | −2.3402 | 1.9331 | 0.0232 | Left-Hippocampus |
| 15 | −0.5499 | 1.5192 | 0.1244 | 1.9565 | 0.0323 | ctx-lh-parsorbitalis |

The results of analysis of the whole brain and 101 areas also show that volume reduction of the whole brain and the hippocampus tended to be suppressed in the Compound A low dose group compared to the placebo group (Nos. 6 and 14 in Table 2).

The same tendency as in the low dose group was observed in the Compound A high dose group.

Test Example 2

Multicenter Randomized Double-Blind Early Phase II Placebo-Controlled Trial for Assessing Effectiveness and Safety of Compound A in Mild to Moderate AD Patients Patients were screened in a period from 28 days before treatment assignment to the assignment based on the following selection criteria. Patients matched (373 patients) were randomly divided into the following 2 groups and the trial was started.
Subject (Selection Criteria):
Patients who were probable AD and over or 50 years old or older and 90 years old or younger at the time of obtaining consent of screening.
Patients with an MMSE score of 15 to 24 at the time of screening
Patients with a Modified Hachinski Ischemia Scale score of 4 or less
Patients who have been treated with a donepezil hydrochloride for at least 6 months before the baseline and with a stable dose thereof for 3 months before the baseline.
Patients whose brain MRI or CT results match AD at the time of screening Organization of groups:
(1) Active drug group: 224 mg of a test compound (160 mg in terms of Compound A) was orally administered once a day for 52 weeks (176 patients)
(2) Placebo group: placebo was orally administered once a day for 52 weeks (178 patients) Method of assessment:
Volumetric MRI
Brain volume of subjects was measured by vMRI scan at the screening and after 52 weeks, and the volume change of the whole brain and the hippocampus of the subjects were quantified to assess brain atrophy based on the change from the screening.
Statistical Analysis:
The mean amount of volume change of the whole brain and the hippocampus after 52 weeks from the baseline, standard deviation and the difference from the placebo group were calculated.
Results: Shown Below
Change in brain volume obtained by vMRI scan at week 52 from the baseline is shown in Table 3, FIG. 3 and FIG. 4.

Preparation Example 1

0.9726 g of magnesium stearate (magnesium stearate, Merck) was added to 174.03 g of maleate of Compound A and the mixture was mixed for 30 minutes. The mixed powder was compression-molded by a roller compactor (TF-LABO (roll pressure 3 MPa), Freund Corporation), and the solid obtained by molding was granulated. 49.51 g of lactose (FlowLac 90, Meggle Japan), 16.50 g of crystalline cellulose (CEOLUS PH302, Asahi Kasci Chemicals) and 6.67 g of croscarmellose sodium (Primellose, DMV Japan) were each sieved through a sieve with an opening of 850 μm and added to 60.0 g of the resulting granulated powder, and the mixture was mixed for 10 minutes. 0.6667 g of magnesium stearate was added to the mixed powder and the mixture was mixed for 30 minutes. The mixed powder was tableted by a tableting machine (HT-P18A, Hata Tekkosho) at a tableting pressure of about 12 kN using a pestle having a double rounded surface with a tablet diameter of 8.5 mm to obtain round uncoated tablets each weighing 250 mg. The uncoated tablets were coated with 8 mg of a coating agent per tablet using a film coater DRC-200 (Powrex), and then a small amount of carnauba wax (Polishing Wax-105, Nippon Wax) was added thereto to give film-coated tablets.

Preparation Example 2

60.90 g of mannitol (Parteck M200, Merck) and 3.60 g croscarmellose sodium were added to 53.70 g of maleate of Compound A and the mixture was mixed for 10 minutes. 1.80 g of magnesium stearate was added to the mixed powder and the mixture was mixed for 30 minutes. The mixed powder was tableted at a tableting pressure of about 10 kN using a pestle having a double rounded surface with a tablet diameter of 8.5 mm to obtain round uncoated tablets each weighing 250 mg. The uncoated tablets were coated with 8 mg of a coating agent (Opadry 03F44057, 00F440000 (hypromellose 2910: 71.5%, Macrogol 6000: 14.166%, talc: 7.167%, titanium oxide: 7.067%, iron sesquioxide: 0.1%), Colorcon Japan LLC) per tablet, and then a small amount of carnauba wax was added thereto to give film-coated tablets.

Preparation Example 3

11.11 g of magnesium stearate was added to 1988.89 g of maleate of Compound A and the mixture was mixed for 30 minutes. The mixed powder was compression-molded by a roller compactor, and the solid obtained by molding was granulated. To 107.13 g of the resulting granulated powder were added 26.21 g of mannitol, 7.50 g of ethyl cellulose (ETHOCEL 100FP Premium, The Dow Chemical Company), 3.75 g of crystalline cellulose (CEOLUS KG-1000, Asahi Kasei Chemicals), 3.75 g of crospovidone (Kollidon CL-SF, BASF) and 0.75 g of croscarmellose sodium, and the mixture was mixed for 30 minutes. 0.90 g of magnesium

TABLE 3

| Group | Number of cases/statistics | Brain volume | |
|---|---|---|---|
| | | Whole brain (mL) | Hippocampus (mL) |
| Low dose group | Number of cases | 7 | 7 |
| | Mean change (standard deviation) | −3.83 (3.14) | −0.21 (0.12) |
| | Difference from placebo group | 3.41 | 0.09 |
| Placebo group | Number of cases | 10 | 10 |
| | Mean change (standard deviation) | −7.24 (4.79) | −0.30 (0.16) |

For the change in the volume of the whole brain and the hippocampus at week 52 from the baseline, volume reduction tended to be smaller in the Compound A group than in the placebo group.

stearate was added to the mixed powder and the mixture was mixed for 5 minutes. The mixed powder was tableted at a tableting pressure of about 7 kN using a pestle having a double rounded surface with a tablet diameter of 8.5 mm to obtain round uncoated tablets each weighing 315 mg. The uncoated tablets were coated with 9 mg of a coating agent per tablet, and then a small amount of carnauba wax was added thereto to give film-coated tablets.

The invention claimed is:

1. A method of preventing or treating brain atrophy in humans, comprising administering 1-(3-(2-(1-benzothiophen-5-yl)ethoxy)propyl)azetidin-3-ol or a salt thereof to a human patient.

2. The method for preventing or treating brain atrophy according to claim 1, wherein 1-(3-(2-(1-benzothiophen-5-yl)ethoxy)propyl)azetidin-3-ol or a salt thereof is orally administered once a day in a dose of 100 mg to 400 mg in terms of 1-(3-(2-(1-benzothiophen-5-yl)ethoxy)azetidin-3-ol per administration.

3. The method for preventing or treating brain atrophy according to claim 1, wherein 1-(3-(2-(1-benzothiophen-5-yl)ethoxy)propyl)azetidin-3-ol or a salt thereof is orally administered once a day in a dose of 160 mg or 320 mg in terms of 1-(3-(2-(1-benzothiophen-5-yl)ethoxy)propyl)azetidin-3-ol per administration.

4. The method for preventing or treating brain atrophy according to claim 1, wherein the method is for administration to a human patient with a neurodegenerative disease.

5. The method for preventing or treating brain atrophy according to claim 1, wherein the method is for administration to a human patient with Alzheimer's disease, Probable Alzheimer's disease, Possible Alzheimer's disease, Preclinical Alzheimer's disease, Prodromal Alzheimer's disease, mild cognitive impairment due to Alzheimer's disease (MCI due to AD) or mild cognitive impairment.

6. The method for preventing or treating brain atrophy according to claim 1, wherein the method is for administration to a human patient with Alzheimer's disease, mild cognitive impairment due to Alzheimer's disease (MCI due to AD) or mild cognitive impairment.

7. The method for preventing or treating brain atrophy according to claim 1, wherein the method is for administration to a human patient with Alzheimer's disease.

8. The method for preventing or treating brain atrophy according to claim 1, wherein the method is for administration to a human patient with mild cognitive impairment due to Alzheimer's disease (MCI due to AD).

* * * * *